United States Patent [19]
Aust et al.

[11] Patent Number: 5,885,288
[45] Date of Patent: Mar. 23, 1999

[54] SURGICAL INSTRUMENT

[75] Inventors: Gilbert M. Aust, Huntsville, Ala.; Timothy E. Taylor, Attleboro, Mass.

[73] Assignee: Endius Incorporated, Plainville, Mass.

[21] Appl. No.: 873,281

[22] Filed: Jun. 11, 1997

Related U.S. Application Data

[63] Continuation-in-part of Ser. No. 248,507, May 24, 1994, Pat. No. 5,454,827, and a continuation-in-part of Ser. No. 505,476, Jul. 21, 1995, Pat. No. 5,618,294.

[51] Int. Cl.⁶ .................................................. A61B 17/28
[52] U.S. Cl. ............................................ 606/170; 604/22
[58] Field of Search .............................. 606/1, 170, 171, 606/180, 159; 604/22; 124/750–755

[56] References Cited

U.S. PATENT DOCUMENTS

| | | |
|---|---|---|
| 3,470,876 | 10/1969 | Barchilon . |
| 3,605,725 | 9/1971 | Bentov . |
| 5,354,311 | 10/1994 | Kambin et al. .......................... 606/170 |
| 5,540,706 | 7/1996 | Aust et al. ............................... 606/170 |

FOREIGN PATENT DOCUMENTS

| | | |
|---|---|---|
| 030128A1 | 2/1989 | European Pat. Off. . |
| 2662778 | 5/1990 | France . |
| 3920706A1 | 1/1991 | Germany . |
| 4136861A1 | 5/1993 | Germany . |
| 4204051A1 | 8/1993 | Germany . |
| O9300048 | 1/1993 | WIPO . |
| O9304634 | 3/1993 | WIPO . |
| 9320760 | 10/1993 | WIPO . |

*Primary Examiner*—William Lewis
*Attorney, Agent, or Firm*—Tarolli, Sundheim, Covell Tummino & Szabo

[57] ABSTRACT

A surgical instrument includes a manually engageable handle and a first stem section having a longitudinal axis and extending from the handle. A tip portion of the surgical instrument has a suction port for applying suction to tissue and a fluid outlet port for directing fluid to tissue. A second stem section is connected between the first stem section and the tip portion and has at least a portion which is bendable. The second stem section supports the tip portion for movement between a plurality of orientations relative to the axis and to the first stem section. The surgical instrument includes means for bending the bendable portion of the second stem section to change the orientation of the tip portion of the surgical instrument relative to the axis and to the first stem section from a first orientation to a second orientation. The means for enabling bending movement moves the tip portion through a plurality of arcuate paths which are of different lengths and which are spaced apart from each other along the longitudinal axis.

14 Claims, 4 Drawing Sheets

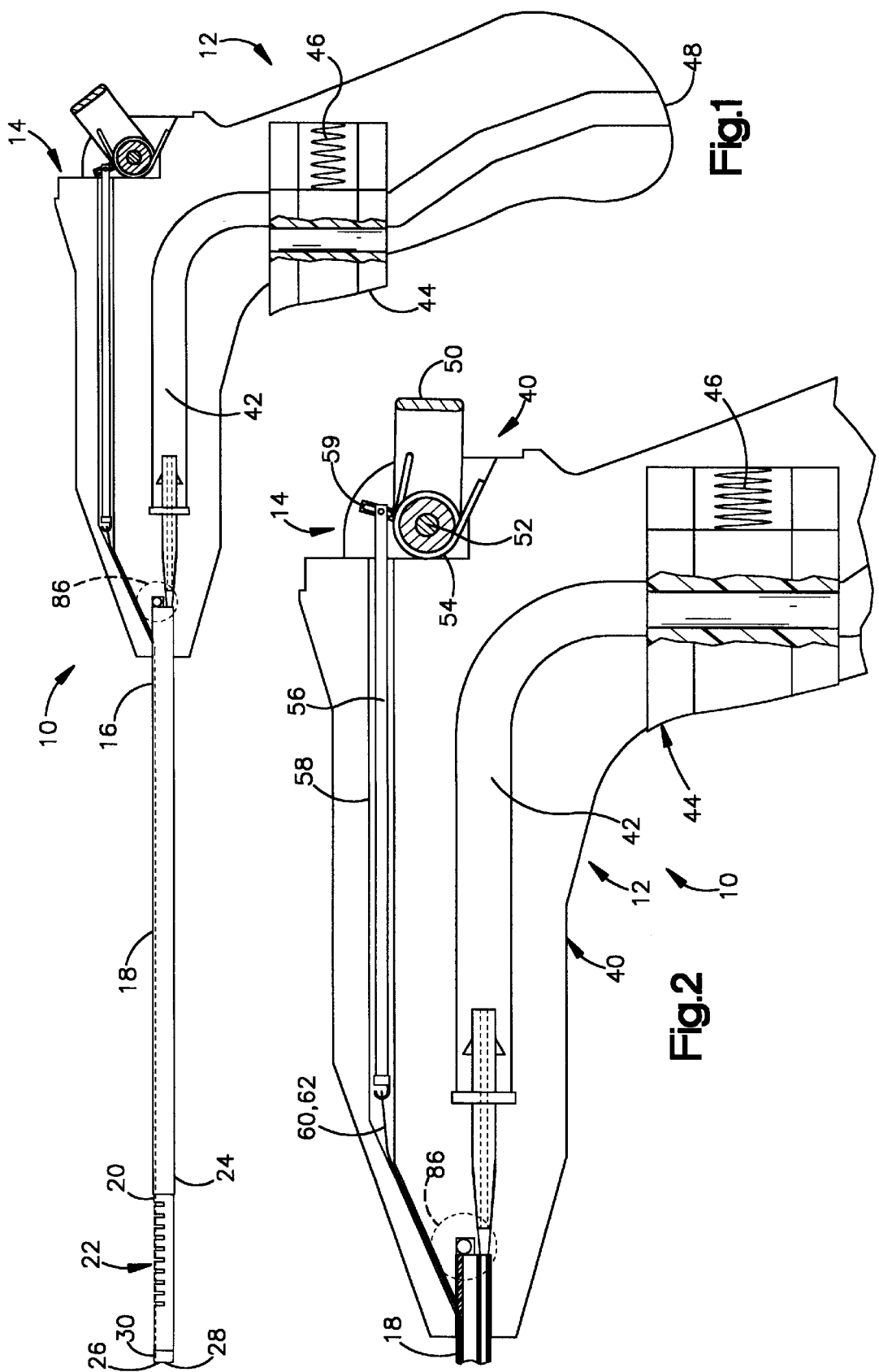

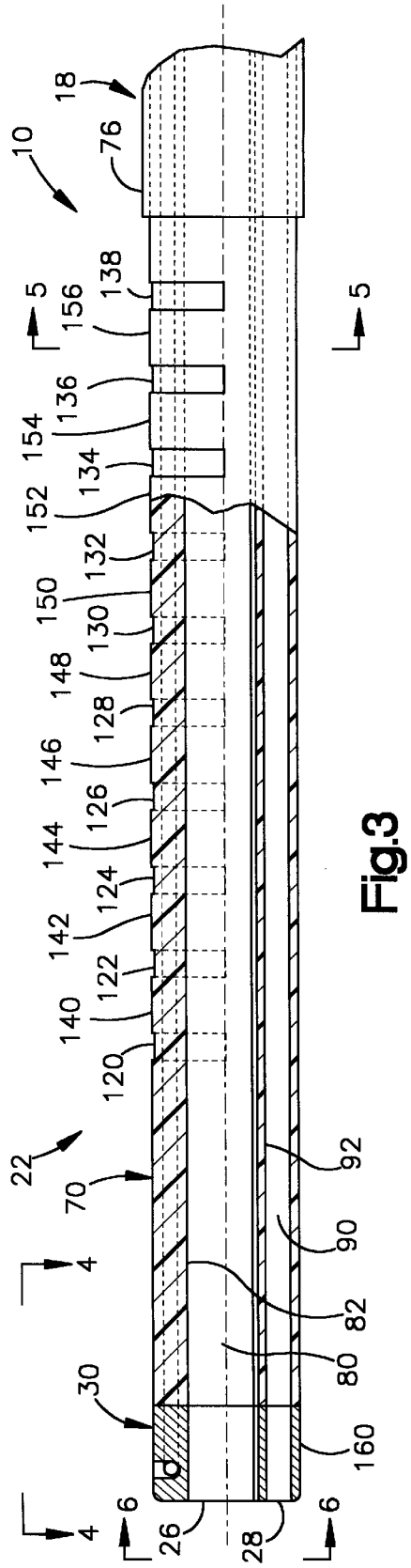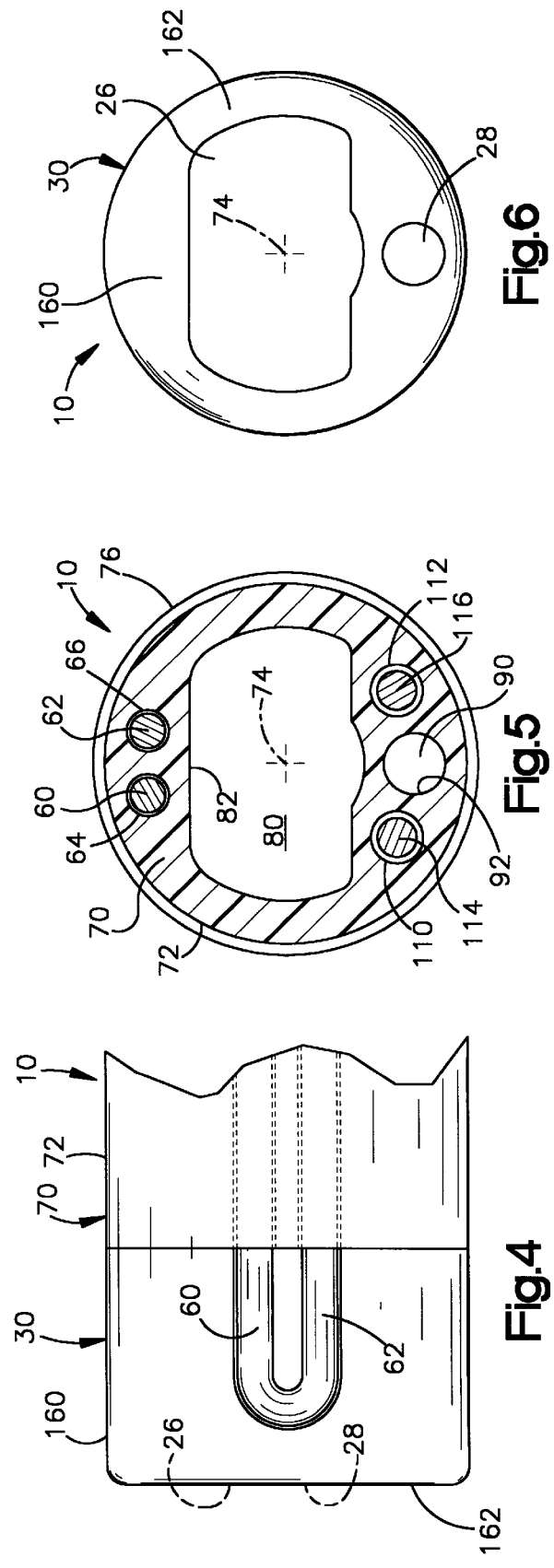

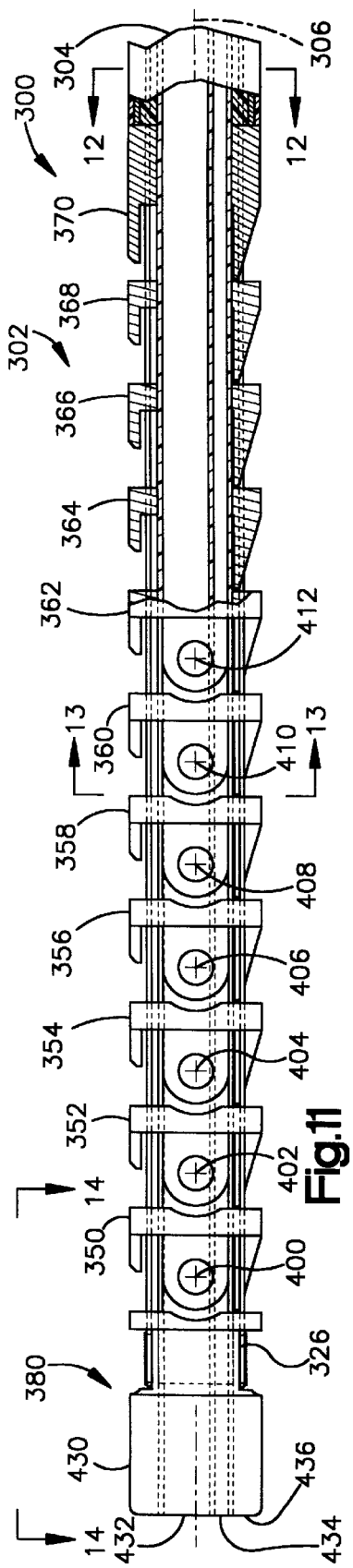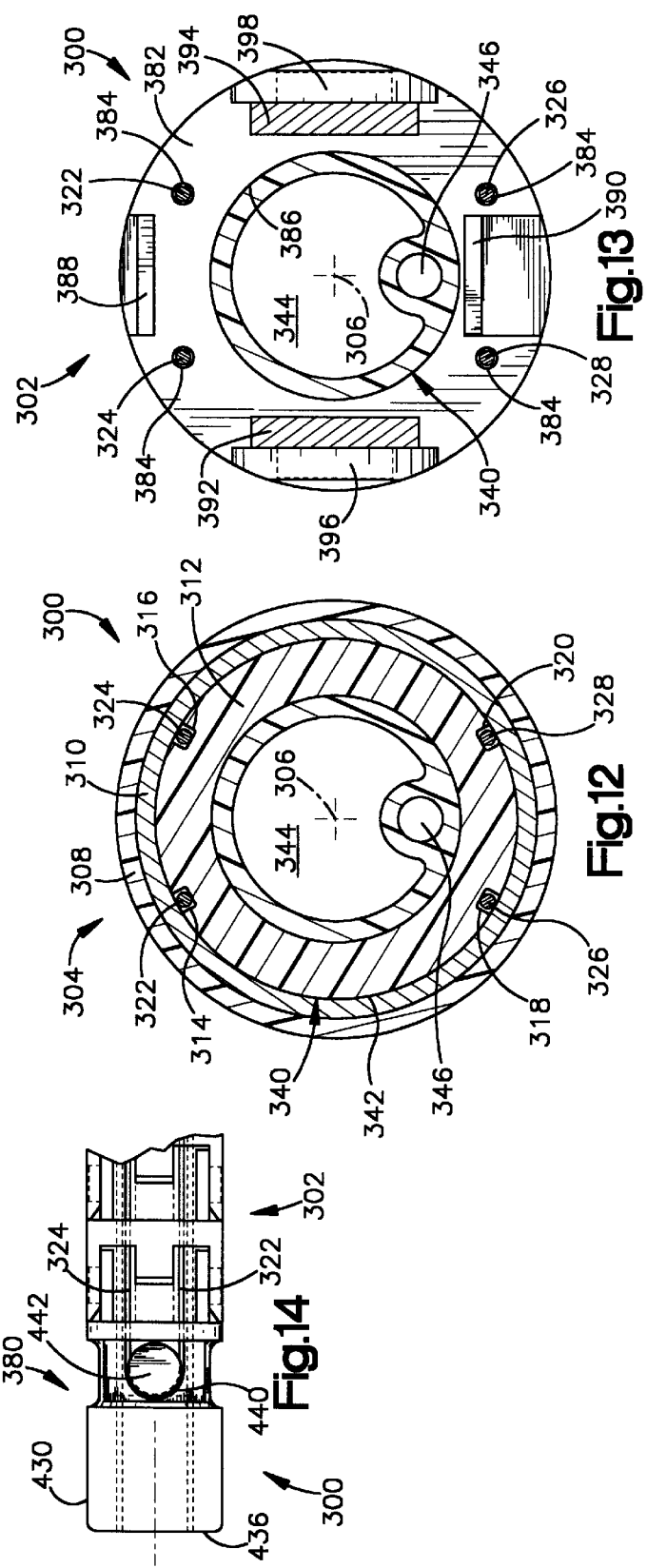

SURGICAL INSTRUMENT

RELATED APPLICATION

This application is a continuation-in-part of U.S. patent application Ser. No. 08/248,507, filed May 24, 1994, U.S. Pat. No. 5,454,827 by the same inventors. This application is also a continuation-in-part of U.S. patent application Ser. No. 08/505,476, filed Jul. 21, 1995 U.S. Pat. No. 5,618,294, by the same inventors.

BACKGROUND OF THE INVENTION

The present invention relates to a surgical instrument and, more particularly, to an endoscopic surgical instrument which may be used for suction and/or irrigation of tissue and bodily fluids.

SUMMARY OF THE INVENTION

The present invention is a surgical instrument comprising a manually engageable handle and a first stem section having a longitudinal axis and extending from the handle. A tip portion of the surgical instrument has a suction port for applying suction to tissue and a fluid outlet port for directing fluid to tissue. A second stem section is connected between the first stem section and the tip portion and has at least a portion which is bendable. The second stem section supports the tip portion for movement between a plurality of orientations relative to the axis and to the first stem section. The surgical instrument comprises means for bending the bendable portion of the second stem section to change the orientation of the tip portion of the surgical instrument relative to the axis and to the first stem section from a first orientation to a second orientation. The means for enabling bending movement moves the tip portion through a plurality of arcuate paths which are of different lengths and which are spaced apart from each other along the longitudinal axis.

BRIEF DESCRIPTION OF THE DRAWINGS

Further features of the present invention will become apparent to those skilled in the art to which the present invention relates from reading the following specification with reference to the accompanying drawings, in which:

FIG. 1 is a schematic side elevational view of a surgical instrument constructed in accordance with a first embodiment of the present invention;

FIG. 2 is an enlarged view of a portion of the surgical instrument of FIG. 1;

FIG. 3 is an enlarged schematic side elevational view of a movable stem section of the surgical instrument of FIG. 1;

FIG. 4 is a view taken along line 4—4 of FIG. 3;

FIG. 5 is a sectional view taken along line 5—5 of FIG. 3;

FIG. 6 is a fragmentary plan view taken along line 6—6 of FIG. 3;

FIG. 11 is a view similar to FIG. 3 of a portion of a surgical instrument which is constructed in accordance with a second embodiment of the present invention;

FIG. 12 is a sectional view taken along line 12—12 of FIG. 11;

FIG. 13 is a sectional view taken along line 13—13 of FIG. 11; and

FIG. 14 is a view similar to FIG. 4 taken along line 14—14 of FIG. 11.

DESCRIPTION OF PREFERRED EMBODIMENTS

Figure 7:
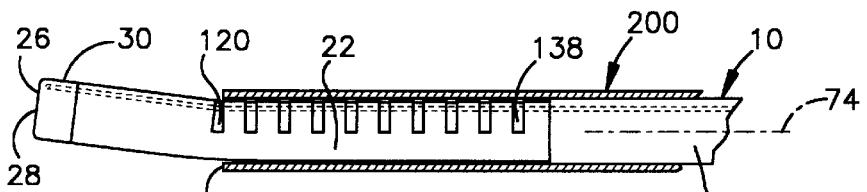
FIG. 7 is a schematic view of a portion of FIG. 1 showing the movable stem section associated with a cannula and bent in a first direction.

The present invention relates to a surgical instrument and in particular to a surgical instrument which may be used for suction and/or irrigation of tissue. The present invention is applicable to various surgical instrument constructions. As representative of the present invention, FIGS. 1–10 illustrate a surgical instrument 10.

The surgical instrument 10 includes generally a handle 12 with an actuator assembly 14. A proximal end portion 16 of a first stem section or rigid stem section 18 is fixed to the handle 12. A proximal end portion 20 of a second stem section or movable stem section 22 is connected with a distal end portion 24 of the rigid stem section 18. A suction port or aspiration port 26, and a fluid outlet port or irrigation port 28, are located on a distal end portion or tip portion 30 of the movable stem section 22.

The handle 12 of the surgical instrument 10 includes a main body portion 40 having a pistol grip configuration which is configured to be manually gripped by a person's hand. An irrigation fluid passage 42 is formed in the main body portion 40 of the handle 12. Irrigation fluid such as water or saline solution can be supplied to the surgical instrument 10 by a known fluid source connected at a fluid inlet opening 48.

A portion of the irrigation fluid passage 42 extends through a manually engageable trigger 44. The trigger 44 is supported in the main body portion 40 of the handle 12 for sliding movement relative to the main body portion. A spring 46 connected between the trigger 44 and the main body portion 40 of the handle 12 biases the trigger to an unactuated position shown in FIG. 1. When the trigger 44 is in the unactuated position as shown in FIG. 1, flow of irrigation fluid through the passage 42 is blocked. When the trigger 44 is in the actuated position as shown in FIG. 2, flow of irrigation fluid through the passage 42 is enabled.

The actuator assembly 14 is mounted in the main body portion 40 of the handle 12. The actuator assembly 14 is illustrated only schematically. It should be understood that other types of actuator assemblies can be substituted. Thus, the actuator assembly 14 is illustrative of the various types of actuator assemblies which can be used to provide the actuation force for bending the movable stem section 22 of the surgical instrument 10 in the manner illustrated.

The actuator assembly 14 (FIGS. 1 and 2) includes a manually engageable deflection control lever 50 which projects from the main body portion 40 of the handle 12. The deflection control lever 50 is supported by a pivot pin 52 for pivotal movement relative to the main body portion 40 of the handle 12. A return spring 54 connected between the deflection control lever 50 and the main body portion 40 of the handle 12 biases the deflection control lever into the unactuated position shown in FIG. 1.

A pull rod 56 extends through a passage 58 in the main body portion 40 of the handle 12. The pull rod 56 is connected via a link 59 with the deflection control lever 50. The proximal ends of two deflection control wires 60 and 62 are connected for movement with the pull rod 56. The two wires 60 and 62 comprise the end portions of a single control wire the central portion of which is looped around the tip portion 30 of the surgical instrument 10 as described below. The deflection control wires 60 and 62 extend from the pull rod 56 into respective deflection control wire passages 64 and 66 in the rigid stem section 18. The deflection control wires 60 and 62, in a manner described below, pass through the rigid stem section 18 and the movable stem section 22, and are connected with the tip portion 30 of the surgical instrument 10.

The rigid stem section 18 of the surgical instrument 10 is a tubular member which extends between and interconnects the handle 12 and the movable stem section 22. The rigid stem section 18 has a longitudinal central axis 74 which forms a longitudinal central axis of the surgical instrument 10.

The rigid stem section 18 includes a generally cylindrical main body portion 70 (FIG. 5) which is made from a plastic material and which has a cylindrical outer side surface 72. The plastic material is one which exhibits the characteristics of resilience and low bending resistance. One suitable plastic material is SILASTIC® brand polymer which is available from Dow Corning Corporation of Midland, Mich. This polymer is comparable in physical character to milled and compounded rubber prior to vulcanization but containing organosilicon polymers.

In the rigid stem section 18, a metal sheath 76 overlies the main body portion 70. The movable stem section 22 is substantially similar to the rigid stem section 18, with the exceptions that the sheath 76 is not included and that the movable stem section has a series of grooves, described below in detail, for providing flexibility to the movable stem section.

A central passage or suction passage 80 of the main body portion 70 is defined by an inner peripheral surface 82 of the main body portion. The suction passage 80 has an oblong shape generally centered on the axis 74. The proximal end 84 of the suction passage 80 is formed as a suction connection 86 for connection with standard suction (aspiration) means.

An irrigation passage 90 of the main body portion 70 is defined by a circular inner peripheral surface 92 of the main body portion. The irrigation passage 90 is disposed below the suction passage 80 (as viewed in FIGS. 3, 5 and 6). The irrigation passage 90 is connected in fluid communication with the irrigation fluid passage 42 in the handle 12.

The deflection control wire passages 64 and 66 extend through and are formed in the main body portion 70, at a location above the suction passage 80 (as viewed in FIGS. 3 and 5–6). The deflection control wires 60 and 62 extend from the pull rod 56 through the control wire passages 64 and 66 in the main body portion 70.

A pair of support rod passages 110 and 112 are formed in the main body portion 70, spaced apart on opposite sides of the irrigation passage 90. A pair of metal support rods 114 and 116 are disposed in the support rod passages 110 and 112 and extend parallel to the central axis 74 when the surgical instrument 10 is linear. The support rods 114 and 116 extend in both the rigid stem section 18 and the movable stem section 22.

The support rods 114 and 116 are made from a flexible, resilient metal. The preferred material is TINEL® brand metal, which is a superelastic nickel-titanium alloy available from Raychem Corporation of Menlo Park, Calif. After an apparent plastic deformation to strain the metal more than ten times the elastic limit of stainless steel, a Tinel shape-memory alloy returns to its original shape each time the deforming load is released. No temperature change is required to induce this superelasticity. Also, the Tinel material does not take a permanent set when bent to a position off the central axis 74.

The support rods 114 and 116 exhibit a self-centering effect and thus tend to attempt to return the movable stem section 22 of the surgical instrument 10 to its linear condition, as illustrated in FIG. 1, after it is bent off the central axis 74. Thus, the support rods 114 and 116 may obviate a deflection control return spring such as the return spring 54 (FIG. 2). The support rods 114 and 116, because they are made from metal, also provide a substantial amount of structural support for the rigid stem section 18 of the surgical instrument 10.

The outer surface 72 of the plastic main body portion 70 of the surgical instrument 10 is circumferentially relieved or indented or grooved at predetermined locations to control the bending characteristics of the movable stem section 22 of the surgical instrument. Specifically, a series of circumferential grooves 120–138 is formed in the outer surface 72 of the main body portion 70.

Each one of the grooves 120–138 extends perpendicular to the axis 74. The grooves 120–138 define between them a series of links 140–156 of the movable stem section 22 of the surgical instrument 10. The grooves 120–138 act as pivot joints defining pivot axes between the links 140–156. The pivot axes all extend parallel to each other. The grooves 120–138, and thus the pivot joints defined by the grooves, are bendable independently of each other. The bending resistance of the main body portion 70 and, thereby, of the movable stem section 22 of the surgical instrument 10, is controlled by the depth (radial extent), width (axial extent), and axial placement of the grooves 120–138.

In the illustrated embodiment, all the grooves 120–138 have the same arcuate cross-sectional configuration and have the same first depth, i.e., radial extent. The grooves 120–138 are spaced apart by a first distance along the length of the movable stem section 22 of the surgical instrument 10. The first distance is relatively small and, accordingly, the bending resistance of the main body portion 70 is relatively low.

In contrast, other grooves (not shown) may be provided which are spaced apart by a second distance, different from the first distance, along the length of the movable stem section 22 of the surgical instrument 10. If the second distance is substantially greater than the first distance, this tends to increase the bending resistance of the main body portion 70, to a level which is relatively high and is greater than the bending resistance of the main body portion at the location of the grooves 120–138.

As another example, other grooves (not shown) may be provided on the movable stem section 22 of the surgical instrument 10 which are deeper than the grooves 120–138, that is, which have a radial extent which is greater than the depth of the grooves 120–138. Also, grooves (not shown) may be provided which have a width (axial extent) which is greater than the width of the grooves 120–138. These types of grooves can tend to decrease the bending resistance of the main body portion 70 to a level which is less than the bending resistance at the grooves 120–138.

The distal end portion or tip portion 30 of the surgical instrument 10 comprises a metal tip 160 which is bonded or otherwise secured to the distal end of the main body portion 70. The deflection control wires 60 and 62 extend into the tip 160 and form a loop 162. The suction passage 80 extends into and through the metal tip 160 and terminates in the suction port 26. The irrigation passage 90 extends into and through the metal tip 160 and terminates in the irrigation port 28. The suction port 26 and the irrigation port 28 are formed as openings in a distal end surface 164 of the metal tip 160 of the surgical instrument 10. It should be understood that the suction port 26 and the irrigation port 28 could be formed in any part of the surgical instrument 10 which is supported for movement on the movable stem section 22. Therefore, the terms "distal end portion" and "tip portion", which refer to that part of the surgical instrument having the suction port and the irrigation port, should be read to encompass any such structure or configuration.

The surgical instrument 10 is typically used in association with a cannula 200 (FIGS. 7–10 ) having an open distal end 202. The cannula 200 is a known tubular member of any suitable construction which is used, in a known manner, to provide an open path through body tissue to the operating site.

Once the cannula 200 is properly positioned, the surgical instrument 10 is inserted axially through the cannula until at least the distal end portion 30 of the surgical instrument protrudes from the distal end 202 of the cannula 200. A predetermined amount of the movable stem section 22 of the surgical instrument 10 may also protrude from the distal end 202 of the cannula 200, as described below.

When the surgical instrument 10 is thus inserted through the cannula 200, and the deflection control lever 50 is moved, the movable stem section 22 of the surgical instrument is bendable at about the location of the distal end 202 of the cannula 200, to position the tip portion 30 in the desired location. When a known source of suction is connected with the suction connection 86 (FIG. 1), suction can be drawn through the suction passage 80 when the movable stem section is in any of the orientations shown in FIGS. 1–10. Also, when a known source of irrigation fluid such as water or saline is connected with the irrigation fluid inlet port 48 (FIG. 1), irrigation fluid can be pumped through the irrigation passage 90 when the movable stem section is in any of the orientations shown in FIGS. 1–10.

The distal end 202 of the cannula 200 acts as a fulcrum about which the movable stem section 22 of the surgical instrument 10 bends. Depending on how much of the surgical instrument 10 protrudes from the distal end 202 of the cannula 200, the surgical instrument bends through different arcuate paths of different lengths, at different locations along the length of the movable stem section.

The surgical instrument 10 bends at different locations along the length of the movable stem section 22, when the deflection control lever 50 is moved, because of the restrictions on its movement resulting from the presence of the cannula 200. Thus, the movable stem section 22 of a surgical instrument 10 in accordance with the present invention can be bent at the same angle, relative to the longitudinal axis 74 of the rigid stem section 18, at more than one location along the length of the movable stem section.

For example, as shown in FIG. 7, if only the most distal groove 120 of the movable stem section 22 protrudes from the distal end 202 of the cannula 200, the surgical instrument 10 bends, as shown in FIG. 7, at the approximate location of the groove 120. The tip portion 30 of the surgical instrument as shown in FIG. 7 extends at a relatively small angle to the central axis 74, at the approximate location of the groove 120. The movable stem section 22 of the surgical instrument 10 bends in a first arcuate path, of a first length, at a first location along the axis 74.

Figure 8:
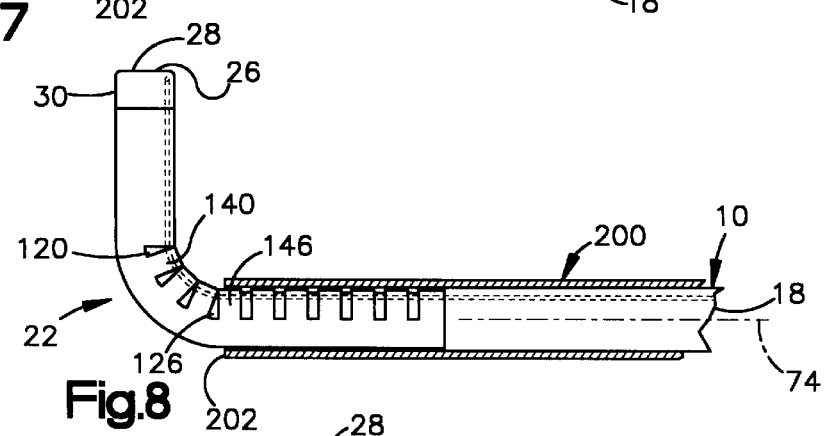
FIG. 8 is a view similar to FIG. 7 showing the movable section bent further and in a second direction.

In another example, if the first four link portions 140–146 of the movable stem section 22 protrude from the distal end 202 of the cannula 200, as shown in FIG. 8, the surgical instrument 10 bends in a manner as shown in FIG. 8. The tip portion 30 of the surgical instrument 10 extends at an angle of 90° to the central axis 74, at the approximate location of the groove 126. The movable stem section 22 of the surgical instrument 10 bends in a second arcuate path, of a length different from the first length, at a second location along the axis 74.

Figure 9:
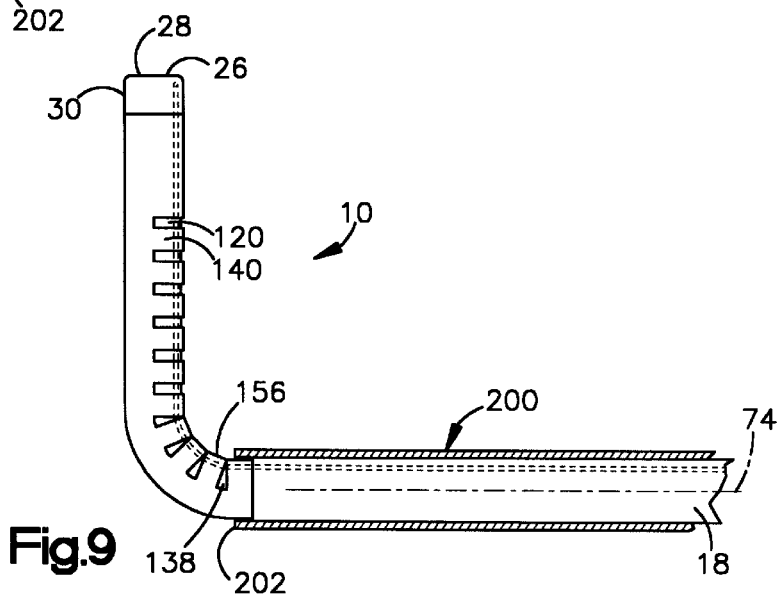
FIG. 9 is a view similar to FIG. 7 showing the movable section of the surgical instrument bent at a different location along its length.

In a third example, if all of the link portions 140–156 protrude from the distal end 202 of the cannula 200, as shown in FIG. 9, the surgical instrument 10 bends in a manner as shown in FIG. 9. The distal end portion 30 of the surgical instrument 10 extends at an angle of 90° to the central axis 74, at the approximate location of the groove 138. This 90° bending location is spaced apart from the 90° bending location shown in FIG. 8 by a substantial distance along the length of the movable stem section 22 of the surgical instrument 10. The movable stem section 22 of the surgical instrument 10 bends in a third arcuate path, of a third length different from the first and second lengths, at a third location along the axis 74.

Thus, the positioning of the surgical instrument 10 relative to the cannula 200 can control and determine the bending location. It should be noted that, instead of a cannula, the wall of a body space can be used to control the bending. For example, the tough outer wall of a spinal disc, or a bone defining a body cavity such as a sinus, can act as the fulcrum for bending the movable stem section 22 of the surgical instrument 10 to perform work within the spinal disc. Any of the embodiments described herein can be used with a cannula in the manner described above.

Figure 10:
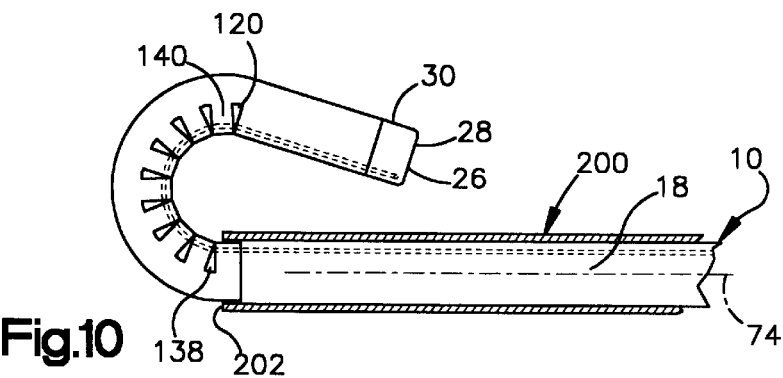
FIG. 10 is a view similar to FIG. 7 showing the movable section bent to an angle greater than 180°.

Further, the movable stem section 22 of the surgical instrument 10 can bend up to 90° to 180°, or more, at many locations along its length depending on the range of bending movement which is available at each groove 120–138. For example, as shown in FIG. 10, the movable stem section 22 is bent through an arc which has a circumferential extent of greater than 180°.

The amount of bending of the movable stem section 22 of the surgical instrument 10 is controlled by the amount of tension on the deflection control wires 60 and 62 the amount of movement of the deflection control lever 50. Because of the ability of the surgical instrument 10 to bend at 90° or more at almost any selected location along the length of the movable stem section 22, the distal end portion 30 of the surgical instrument, including the suction port 26 and the irrigation port 28, can be positioned and used in substantially any position outside the distal end 202 of the cannula 200.

This is enhanced by the fact that no portions of the movable stem section 22 of the surgical instrument 10 extend radially outward of the plastic body portion 70 and so the surgical instrument can be "pistoned" or moved axially with little restriction even when the movable stem section 22 is bent at 90° or more. These features provide a much larger operating field than is available with a surgical instrument which bends to 90° at only one location along its length.

It should be understood that the present invention is not limited to bending movement of, for example, 90° or more. Thus, the movable stem section 22 might be independently bendable at, say, 18° at each of ten different locations along its length, thus providing a total of 180° of bending movement.

FIGS. 11–14 illustrate a portion, i.e., the movable stem section 302, of a surgical instrument 300 which is constructed in accordance with a second embodiment of the present invention. Components of the surgical instrument 300 which are shown incompletely or not at all, such as the handle assembly, are the same as or similar to the corresponding components in the surgical assembly 10.

A rigid stem section 304 (FIG. 12) of the surgical instrument 300 has a longitudinal central axis 306. The axis 306 forms a longitudinal central axis of the surgical instrument 300. The rigid stem section 304 includes an outer plastic sheath 308 which overlies an intermediate metal tube 310. An intermediate plastic sheath 312 is disposed radially inward of the metal tube 310. The plastic sheath 312 has four deflection control wire passages 314, 316, 318, and 320 through which four deflection control wires 322, 324, 326, and 328 extend. The control wires 322–328 are operatively connected with a deflection control lever (not shown) which is similar to the lever 50 (FIGS. 1 and 2).

The rigid stem section 304 (FIG. 12) also includes a plastic body portion 340. The plastic body portion 340 is a flexible tubular member which extends within the intermediate plastic sheath 312. The plastic body portion 340 is preferably made from a polymeric material such as polytetrafluoroethylene which is flexible and resilient. The plastic body portion 340 has a generally cylindrical configuration with an outer periphery 342. A suction passage 344 and an irrigation passage 346 are formed in and extend through the plastic body portion 340. The suction passage 344 and the irrigation passage 346 are connected with, respectively, a suction source and a source of irrigation fluid (both not shown).

The movable stem section 302 of the surgical instrument 300 is made of a plurality of links 350–370 which are pivotally interconnected to enable controlled movement of a distal end portion or tip portion 380 of the surgical instrument to a plurality of positions off the axis 306. Each link 350–370 is preferably made from a metal such as stainless steel and includes a radially extending wall portion 382 having four deflection control wire passages 384 through which the deflection control wires 322–328 extend.

The wall portion 382 of each link 350–370 also includes a circular central opening 386 centered on the axis 306. The plastic body portion 340 is received in and extends axially through the central openings 386 of the links 350–370.

Upper and lower guide tabs 388 and 390 project axially from the wall portion 382 of each link 350–370 in a direction toward the tip portion 380. On each link 350–370, a pair of pivot pins 392 and 394 are received in socket portions 396 and 398 of the next most proximal link. The pivot pins 392 and 394, and the sockets 396 and 398, form pivot joints which define a plurality of pivot axes 400–412 (FIG. 11). The pivot axes 400–412 extend in a direction perpendicular to the central axis 306 and parallel to each other. Each pivot axis 400–412, in the preferred embodiment, provides about 45° of relative movement between an adjacent pair of links 350–370. This amount of movement could be different in other configurations in accordance with the present invention.

The most proximal link 370 (FIG. 11) of the movable stem section 302 is rigidly connected with the rigid stem section 304. The plastic body portion 340 extends from the rigid stem section 304 into and through the movable stem section 302. The plastic body portion 340 extends axially within the central passages 386 of the links.

The distal end portion 380 of the surgical instrument 300 is rigidly connected with the outermost or most distal link 510 of the movable stem section 302. The distal end portion 380 comprises a metal tip 430 which is connected for movement with the most distal link 350. The suction passage 344 extends into and through the metal tip 430 and terminates in a suction port 432. The irrigation passage 346 extends into and through the metal tip 430 and terminates in a irrigation port 434. The suction port 432 and the irrigation port 434 are formed as openings in a distal end surface 436 of the tip 430 of the surgical instrument 300.

The distal ends of the four deflection control wires 322–328 are connected in a force-transmitting relationship with the metal tip 430. In the preferred embodiment, the two upper (as viewed in FIGS. 11–13) deflection control wires 322 and 324 are formed as one piece which includes an intermediate portion 440 which loops around a post 442 (FIG. 14) on the metal tip 430. In a similar manner, the two lower (as viewed in FIGS. 11–13) deflection control wires 326 and 328 are formed as one piece which includes an intermediate portion which loops around a lower post on the metal tip 430.

Directional movement and positioning of the tip portion 380 of the surgical instrument 10 via the movable stem section 302 are controlled by the tension on the deflection control wires 322–328 as set by an actuator assembly (not shown). Thus, when the deflection control lever of the actuator assembly is in an unactuated position, the movable stem section 302 is linear, and it and the metal tip 430 are aligned along the central axis 306 as shown in FIG. 11.

Movement of the deflection control lever, in a first direction from the unactuated position, tensions the upper deflection control wires 322 and 324 and releases the tension on the lower deflection control wires 326 and 328. This change in the tension on the deflection control wires 322–328 is transmitted through the wires into the metal tip 430. The increase in tension on the upper control wires 322 and 324 acts to attempt to pull the metal tip 430 toward the handle. The movable stem section 302 bends about the pivot axes 400–412 as the links 350–370 pivot relative to the rigid stem section 304. The metal tip 430 thus moves upward (as viewed in FIG. 11) off the central axis 306.

The surgical instrument 300 is usable with a cannula such as the cannula 200 (FIGS. 7–10) and is selectively bendable at different locations along its length in the same manner as the surgical instrument 10. The controlled movement of the metal tip 430 results in controlled movement, and positioning, of the suction port 432 and the irrigation port 434. The movable stem section 302 of the surgical instrument 300 is bendable through an arc which is greater than 180°, relative to the central axis 306 of the surgical instrument. The tubular plastic body portion 340 supports and stabilizes the relatively movable links 350–370. The tubular plastic body portion 340 also has a self-centering effect.

From the above description of the invention, those skilled in the art will perceive improvements, changes and modifications in the invention. Such improvements, changes and modifications within the skill of the art are intended to be covered by the appended claims.

Having described the invention, we claim:

1. A surgical instrument comprising:

a manually engageable handle;

a first stem section having a longitudinal axis and extending from said handle;

a tip portion having a suction port for applying suction to tissue and a fluid outlet port for directing fluid to tissue;

a second stem section connected between said first stem section and said tip portion, said second stem section having at least a portion which is bendable, said second stem section supporting said tip portion for movement between a plurality of orientations relative to said axis and to said first stem section;

means for supporting said tip portion of said surgical instrument on said bendable portion of said second stem section;

means for bending said bendable portion of said second stem section to change the orientation of said tip portion of said surgical instrument relative to said axis and to said first stem section from a first orientation to a second orientation;

said means for bending comprising wires extending through said second stem section and connected to said second stem section;

said bendable portion of said second stem section comprising means for enabling bending movement of said bendable portion to locate said tip portion of said surgical instrument at the same angle relative to said longitudinal axis of said first stem section at more than one location along the length of said bendable portion; and a cannula through which said bendable portion of said second stem section of said surgical instrument is extensible, said cannula having a distal end, said tip portion and a selected amount of said bendable portion of said second stem section of said surgical instrument being extensible from said distal end of said cannula, said distal end of said cannula acting as a fulcrum about which said second stem section bends.

2. A surgical instrument as set forth in claim 1 wherein said bendable portion of said second stem section comprises a plurality of independently movable links and said means for enabling bending movement comprises a plurality of pivot joints, each one of said pivot joints defining a respective pivot axis, each one of said pivot joints interconnecting a pair of adjacent ones of said plurality of links for relative pivotal movement about a respective pivot axis, all of said pivot axes extending generally parallel to each other.

3. A surgical instrument as set forth in claim 2 wherein each one of said links comprises a rigid member having at least one pivot pin which is received in a socket of an adjoining link, said pivot pins and said sockets defining said pivot joints.

4. A surgical instrument as set forth in claim 1 comprising at least one support member extending along and through said bendable portion of said second stem section, said support member being made from a superelastic nickel-titanium alloy.

5. A surgical instrument as set forth in claim 1 wherein said suction port and said irrigation port are both formed as openings in a tip member of said surgical instrument, said surgical instrument further comprising means for defining a suction passage extending along said bendable portion of said second stem section and means for defining an irrigation passage extending along said bendable portion of said second stem section, said suction passage being connected in fluid communication with said suction port and said irrigation passage being connected in fluid communication with said irrigation port, one of said passages being centered on the central axis of said second stem section and the other of said passages being completely offset to one side of said one passage.

6. A surgical instrument as set forth in claim 1 wherein said bendable portion of said second stem section comprises a tubular plastic body portion having surface indentations located at predetermined locations spaced apart along the length of said plastic body portion for decreasing the bending resistance of said plastic body portion at said predetermined locations.

7. A surgical instrument as set forth in claim 1 wherein said means for enabling bending movement comprises a plurality of joints which are spaced along the length of said bendable portions and at which said bendable portion is bendable to locate said tip portion at the same angle relative to said longitudinal axis of said first stem section at each one of said joints, each joint being bendable independently of the other said joint.

8. A surgical instrument as set forth in claim 1 wherein said means for enabling bending movement comprises means for enabling movement of said bendable portion of said second stem section, at more than one location along the length of said bendable portion, into a condition in which said bendable portion has a first segment extending parallel to said axis and a second segment which extends at an angle relative to said axis and to said first stem section.

9. A surgical instrument comprising:

a manually engageable handle;

a first stem section having a longitudinal axis and extending from said handle;

a distal end portion having a suction port for applying suction to tissue and a fluid outlet port for directing fluid to tissue;

a second stem section connected between said first stem section and said distal end portion, said second stem section having at least a portion which is bendable, said second stem section supporting said distal end portion for movement between a plurality of orientations relative to said axis and to said first stem section;

means for supporting said distal end portion on said bendable portion of said second stem section;

means for bending said bendable portion of said second stem section to move said distal end portion through an arcuate path between a plurality of orientations relative to said axis and to said axis and to said first stem section, said means for bending comprising wires extending through said second stem section and connected to said second stem section;

said bendable portion of said second stem section comprising means for enabling bending movement of said bendable portion of said second stem section to move said distal end portion through a plurality of arcuate paths which are of different lengths and which are spaced apart from each other along said longitudinal axis; and a cannula through which said bendable portion of said second stem section of said surgical instrument is extensible, said cannula having distal end, said distal end portion and a selected amount of said bendable portion of said second stem section of said surgical instrument being extensible from said distal end of said cannula, said distal end of said cannula acting as a fulcrum about which said second stem section bends.

10. A surgical instrument as set forth in claim 9 wherein said bendable portion of said second stem section comprises a plurality of independently movable links and said means for enabling bending movement comprises a plurality of pivot joints, each one of said pivot joints defining a respective pivot axis, each one of said pivot joints interconnecting a pair of adjacent ones of said plurality of links for relative pivotal movement about a respective pivot axis, all of said pivot axes extending generally parallel to each other.

11. A surgical instrument as set forth in claim 10 wherein each one of said links comprises a rigid member having at least one pivot pin which is received in a socket of an adjoining link, said pivot pins and said sockets defining said pivot joints.

12. A surgical instrument as set forth in claim 9 comprising at least one support member extending along and through said bendable portion of said second stem section, said support member being made from a superelastic nickel-titanium alloy.

13. A surgical instrument as set forth in claim 9 wherein said suction port and said irrigation port are both formed as openings in a tip member of said surgical instrument, said surgical instrument further comprising means for defining a suction passage extending along said bendable portion of said second stem section and means for defining an irrigation passage extending along said bendable portion of said second stem section, said suction passage being connected in fluid communication with said suction port and said irrigation passage being connected in fluid communication with said irrigation port, one of said passages being centered on the central axis of said second stem section and the other of said passages being completely offset to one side of said one passage.

14. A surgical instrument as set forth in claim 9 wherein said bendable portion of said second stem section comprises a tubular plastic body portion having surface indentations located at predetermined locations spaced apart along the length of said plastic body portion for decreasing the bending resistance of said plastic body portion at said predetermined locations.

* * * * *